United States Patent [19]
Huang

[11] Patent Number: 6,001,782
[45] Date of Patent: Dec. 14, 1999

[54] METAL OVERBASED FATTY AMINES FURTHER DERIVATIZED TO CONTAIN COVALENTLY BOUND SULFER AND/OR PHORPHORUS USEFUL AS ANTIWEAR/ EXTREME PRESSURE ADDITIVES

[75] Inventor: Nai Z. Huang, Highland Hts., Ohio

[73] Assignee: The Lubrizol Corporation, Wickliffe, Ohio

[21] Appl. No.: 09/213,543

[22] Filed: Dec. 17, 1998

[51] Int. Cl.$^6$ .................... C10M 137/06; C10M 135/18
[52] U.S. Cl. .................. 508/420; 508/428; 508/443; 508/444
[58] Field of Search .................. 508/443, 444, 508/420, 428

[56] References Cited

U.S. PATENT DOCUMENTS

| | | | |
|---|---|---|---|
| 3,051,655 | 8/1962 | Barker | 252/49.9 |
| 3,197,405 | 7/1965 | Le Suer | 252/32.7 |
| 3,766,066 | 10/1973 | McMillen | 252/32.7 |
| 3,833,496 | 9/1974 | Malec | 508/444 |
| 4,778,610 | 10/1988 | Horodysky | 252/32.5 |
| 4,919,830 | 4/1990 | Farng et al. | 252/327 |
| 5,019,282 | 5/1991 | Farng et al. | 252/32.7 |
| 5,030,368 | 7/1991 | Okorodudu | 508/428 |
| 5,556,569 | 9/1996 | Huang | 508/545 |
| 5,561,103 | 10/1996 | Tipton | 508/189 |
| 5,652,201 | 7/1997 | Papay et al. | 508/228 |
| 5,670,464 | 9/1997 | Kita et al. | 508/562 |
| 5,693,598 | 12/1997 | Abraham et al. | 508/444 |
| 5,789,357 | 8/1998 | Baranski et al. | 508/444 |

*Primary Examiner*—Ellen M. McAvoy
*Attorney, Agent, or Firm*—James L. Cordek; Joseph P. Fischer

[57] ABSTRACT

An antiwear/extreme pressure composition is disclosed that comprises a metal overbased amine of the structure $$R^1R^2NH(MA)_x$$

wherein $R^1$ and $R^2$ are each independently hydrogen, or a hydrocarbyl group, amino-substituted hydrocarbyl group, hydroxy-substituted hydrocarbyl group, alkoxy-substituted hydrocarbyl group or amino groups wherein the hydrocarbyl group contains from 4 to 50 carbon atoms, provided that $R^1$ and $R^2$ are not both hydrogen, M is a metal, A is carbonate, sulfite, sulfate, thiosulfate, phosphite, phosphate, or mixtures thereof, and x has a value of from 1.1 to 40;

wherein said metal overbased amine is reacted with carbon disulfide to form a sulfur derivative of a metal overbased amine, an epoxide followed by phosphorus pentoxide to form a phosphorus derivative of a metal overbased amine or wherein the sulfur derivative is further reacted with an epoxide followed by phosphorus pentoxide to form a sulfur and phosphorus derivative of a metal overbased amine. A process for preparing antiwear/extreme pressure derivatives of overbased amines is also disclosed.

25 Claims, No Drawings

METAL OVERBASED FATTY AMINES FURTHER DERIVATIZED TO CONTAIN COVALENTLY BOUND SULFER AND/OR PHORPHORUS USEFUL AS ANTIWEAR/ EXTREME PRESSURE ADDITIVES

FIELD OF THE INVENTION

This invention is directed to multifunctional overbased materials and the pathways for preparing them. Non-anionic overbased nucleophilic materials, such as overbased amines, can be further reacted with electron deficient compounds to form highly functionalized overbased materials as multiple performance additives for lubricating oils and fuels. Several innovations are noted with this invention. In contrast to widely used anionic overbased products, the amine overbased material can be further reacted with such compounds as electrophiles to form multifunctional overbased materials. A method is provided to prepare such overbased materials that contain functional groups that would have been unstable during the initial overbasing process if it were present as, for example, dithiocarbamic acids. Finally, these multifunctional overbased materials have the potential to be used as multipurpose additives in lubricating oils and fuels.

BACKGROUND OF THE INVENTION

U.S. Pat. No. 3,051,655 (Barker, Aug. 28, 1962) relates to a metalworking lubricant of a mineral oil of lubricating viscosity and a compound having the structural formula

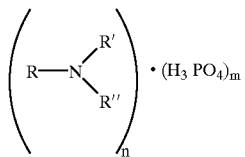

where R is an alkyl group containing a carbon chain possessing from 12 to 30 carbon atoms; R' is selected from the group consisting of H, aminopropyl and ethoxylated aminopropyl groups; R" is selected from the group consisting of H, and polyethoxy groups having 1 to 5 ethylene oxide residue; n is an integer 1 to 3; and m is an integer 1 to 2.

U.S. Pat. No. 3,197,405 (LeSuer, Jul. 27, 1965) is directed to hydroxy-substituted triesters of phosphorothioic acids having the structural formula

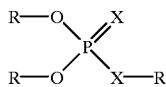

where R is selected from the class consisting of substantially hydrocarbon radicals and hydroxy-substituted substantially hydrocarbon radicals; at least one of the R radicals being a hydroxy-substituted substantially hydrocarbon radical, and X is selected from the class consisting of sulfur and oxygen, at least one of the X radicals being sulfur. The substantially hydrocarbon radicals include aromatic, aliphatic, and cycloaliphatic radicals such as aryl, alkyl, aralkyl, alkaryl and cycloalkyl radicals. Such radicals may contain a polar substituent such as chloro, bromo, jodo, alkoxy, aryloxy, nitro, keto or aldehydro group. In most instances, there should be no more than one such polar group in a radical.

U.S. Pat. No. 3,766,066 (McMillen, Oct. 16, 1973) relates to solid, metal-containing compositions characterized by the ability to be readily and stably dispersed in nonpolar organic liquids and to processes for preparing these compositions. In particular, the reference concerns isolating solid, metal-containing compositions from non-Newtonian colloidal disperse systems. In another aspect, the reference relates to processes for treating non-Newtonian colloidal disperse systems so as to isolate the desired solid, metal-containing compositions.

U.S. Pat. No. 4,778,610 (Horodysky, Oct. 18, 1988) is directed to lubricant compositions that have enhanced friction-reducingiantiwear properties that are prepared by incorporating therein minor amounts of a compound or mixture of compounds which are the reaction product(s) of hydroxyhydrocarbyl hydrocarbyl amines and phosphorus pentoxide.

U.S. Pat. No. 4,919,830 (Farng et al., Apr. 24, 1990) provides lubricant compositions comprising a lubricant and an antioxidant/antiwear amount of a product of reaction comprising a dialkyl dithiocarbamate-derived organic phosphate. Generally speaking, these additive products are made by reacting an alkali-metal hydroxide with a secondary dialkylamine and carbon disulfide in an aqueous/organic media or similarly tialkyl ammonium salts of dithiocarbamates can be made by reacting trialkylamine, dialkylamine and carbon disulfide in non-aqueous media. The products of these reactions are then further reacted with a suitable organic phosphate, for example, tris(2-chloroethyl) phosphate. Accordingly, the reference is also directed to reaction products and to lubricant compositions containing them.

U.S. Pat. No. 5,019,282 (Farng et al., May 28, 1991) is directed to lubricant compositions containing small additive concentrations of phosphorodithioate substituted hydrocarbyl or hydrocarbylene carboxylic anhydride-derived organic esters, amides and amine salts, such as (O,O-di-2-ethylhexyl-S-2-hydroxypropyl) phosphorodithioate substituted dodecenyl succinic acid diesters, amide esters and amine salts that possess excellent antioxidant properties coupled with very good antiwear and antirust activities. Both the phosphorodithioate alcohol moiety and the ester/amine/amide moiety are believed to provide the basis for the synergistic antioxidant activity and each of which are subsequently enhanced by the succinic anhydride coupling moiety. The phosphorodithioate group is believed to contribute additional antiwear properties to these additives.

U.S. Pat. No. 5,030,368 (Okorodudu, Jul. 9, 1991) are directed to amine or metal dithiocarbamate salts having the following structure

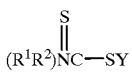

where $R^1$ and $R^2$ are the same or different. $R^1$ and $R^2$ are each a hydrocarbyl group containing from 1 to 36 carbon atoms, having none or at least one heteroatom which can be oxygen, sulfur, or nitrogen. $R^1$ and $R^2$ are selected from alkyl, alkenyl, aryl, aralkyl, alkaryl groups and can contain phenyl, naphthyl, or anthryl substituents; $R^1$, $R^2$ can be a $(CH_n)_m$ group comprising part of an alicyclic or heterocyclic system selected from, for example, pyrrole, pyrrolidine, piperidine, morpholine, etc., where n is 1 or 2 and m is 2 to 8. Y is an ammonium or metal radical.

U.S. Pat. No. 5,556,569 (Huang, Sept. 17, 1996) is directed to organic compounds having at least one hydrocarbyl group and a polar group containing at least one nitrogen, oxygen, or sulfur atom, being free from acidic hydrogen atoms and from functional groups which provide such organic compounds with acidic hydrogen atoms upon hydrolysis, can be overbased by treatment with a metallic base and a low molecular weight acid, to provide useful lubricant additives.

U.S. Pat. No. 5,561,103 (Tipton, Oct. 1, 1996) describes a class of compounds being alkylthio derivatives of alkylethers. The alkylthioalkylethers are used as additives to functional fluids and lubricating fluids to provide a composition of improved functional properties. The thioethers are self-condensation reaction products of thioalkanols and have the general formula

RSCHCHOCHCHSR wherein $R=C_4\text{-}C_{20}$ and $R^1$=hydrogen or hydrocarbyl.

U.S. Pat. No. 5,652,201 (Papay et al., Jul. 29, 1997) relates to oleaginous compositions and additive concentrates therefore having enhanced performance characteristics comprise a) at least one oil-soluble overbased alkali or alkaline earth metal-containing detergent having a TBN of at least 200; and b) one or more oil-soluble boron-free additive compositions formed by heating (i) at least one boron-free oil-soluble ashless dispersant containing basic nitrogen and/or at least one hydroxyl group, with (ii) at least one inorganic phosphorus acid such that a liquid boron-free phosphorus-containing composition is formed.

U.S. Pat. No. 5,670,464 (Kita et al., Sept. 23, 1997) relates to an additive for lubricating oils for diesel engines for land use, marine use, and the like, and to a lubricating oil composition containing the same. More specifically, the reference relates to an additive for lubricating oils for diesel engines which improves the detergency of a lubricating oil and lengthens the life of the lubricating oil, and to a lubricating oil composition containing such an additive.

SUMMARY OF THE INVENTION

An antiwear/extreme pressure composition is disclosed that comprises a metal overbased amine of the structure $R^1R^2NH(MA)_x$ wherein $R^1$ and $R^2$ are each independently hydrogen, or a hydrocarbyl group, amino-substituted hydrocarbyl group, hydroxy-substituted hydrocarbyl group, alkoxy-substituted hydrocarbyl group or amino groups wherein the hydrocarbyl group contains from 4 to 50 carbon atoms, provided that $R^1$ and $R^2$ are not both hydrogen, M is a metal, A is carbonate, sulfite, sulfate, thiosulfate, phosphite, phosphate, or mixtures thereof, and x has a value of from 1.1 to 40;

wherein said metal overbased amine is reacted with carbon disulfide to form a sulfur derivative of a metal overbased amine; said metal overbased amine is reacted with an epoxide followed by phosphorus pentoxide to form a phosphorus derivative of a metal overbased amine or wherein the sulfur derivative of the metal overbased amine is further reacted with an epoxide followed by phosphorus pentoxide to form a sulfur and phosphorus derivative of a metal overbased amine.

A process for preparing antiwear/extreme pressure derivatives of overbased amines is also disclosed, that comprises reacting (A) one mole of a metal overbased amine with
(B) an amine derivatizing agent comprising
  (1) at least one mole of carbon disulfide to form a sulfur derivative of a metal overbased amine,
  (2) at least one mole of an epoxide followed by at least 0.33 moles of phosphorus pentoxide to form a phosphorus derivative of a metal overbased amine, or
  (3) at least one mole of carbon disulfide followed by at least one mole of an epoxide followed by at least 0.33 moles of phosphorus pentoxide to form a sulfur-phosphorus derivative of a metal overbased amine, at a temperature of from ambient up to 150° C.

DETAILED DESCRIPTION OF THE INVENTION

Metal Overbased Amine Derivative

This invention relates to the reaction of (A) a metal overbased amine with (B) an amine derivitizing agent comprising carbon disulfide to form a sulfur derivative of a metal overbased amine; reacting the metal overbased amine with an epoxide and an amine derivitizing agent comprising phosphorus pentoxide to form a phosphorus derivative of a metal overbased amine, or reacting the sulfur derivative of the metal overbased amine with an epoxide and an amine derivitizing agent comprising phosphorus pentoxide to form a sulfur and phosphorus derivative of a metal overbased amine. The metal overbased arnine derivative has the structure $R^1R^2NH(MA)_x$.

(A) The Metal Overbased Amine

It is known to prepare overbased materials using as a substrate an oil-soluble acidic material. The acid functionality can be provided by an acidic group such as a carboxylic, sulfonic or phosphonic acid, by aromatic —OH, or by other groups exhibiting acidic labile hydrogen character, such a alpha- hydrogen-containing lactones. For some materials, the substrate is not itself acidic, but it is capable of being hydrolyzed under overbasing conditions to form an acidic material. For example, certain esters can be overbased because under overbasing conditions the ester will saponify to form the acid. Each of these acidic materials are normally viewed to exist as an anionic component of the salt, when they are employed as the substrate of an overbased material. The present component, in contrast, provides overbased organic materials in which the substrate has no appreciable acidic character and thus cannot be neutralized in the usual sense by a base.

The metal overbased amine is prepared by overbasing an amine. Anines include monoamines and polyamines. The amines can be aliphatic, cycloaliphatic, aromatic, or heterocyclic, including aiphatic-substituted cycloaliphatic, aliphatic-substituted aromatic, aliphatic-substituted heterocyclic, cycloaliphatic-substituted aliphatic, cycloaliphatic-substituted aromatic, cycloaliphatic-substituted heterocyclic, aromatic-substituted aliphatic, aromatic-substituted cycloaliphatic, aromatic-substituted heterocyclic-substituted alicyclic, and heterocyclic-substituted aromatic amines, and can be saturated or unsaturated. The amines can also contain non-hydrocarbon substituents or groups as long as these groups do not impart acidity to the molecule, as described above. Such non-hydrocarbon substituents or groups include lower alkoxy, lower alkyl mercapto, or interrupting groups such as —O— and —S—(e.g., as in such groups as —CH$_2$CH$_2$—X—CH$_2$CH$_2$ where X is —O— or —S—). For example, a useful amine is (N-C$_{16\text{-}18}$ alkyl propylene-diamine, available commercially as Duomeen™O. In general, the amine may be characterized by the formula $R^1R^2HN$ where $R^1$ and $R^2$ are each independently hydrogen or hydrocarbon, amino-substituted hydrocarbon, hydroxy-substituted hydrocarbon, alkoxy-substituted hydrocarbon, or amino groups, provided that $R^1$ and $R^2$ are not both hydrogen.

The amine should contain at least one carbon chain of at least 4 carbon atoms. Preferably, the hydrocarbyl group of this component will contain 8 to 50 and more preferably 12 to 26 carbon atoms. Accordingly, suitable groups include alkyl groups such as butyl, pentyl, hexyl, and preferably higher alkyl groups such as octyl (including 2-ethylhexyl), nonyl, decyl, undecyl, dodecyl, and similar higher alkyl groups e.g. 14, 16, 18, 20, 24, 26, or more carbon atoms. Both straight chain and branched groups can be used. Most such amines are commercially available. For example, N-alkyl trimethylenediamine is available from Akzo under the names Duomeen T™ and Duomeen C™. The alkyl groups can be substituted with other functional groups if desired, provided, however, that such functional groups do not provide any significant amount of acidic hydrogen character to the compound, as discussed above.

Monamines include mono-aliphatic and di-aliphatic substituted amines wherein the aliphatic group can be saturated or unsaturated and straight or branched chain. Thus, they are primary or secondary aliphatic amines. Such amines include, for example, mono- and di-alkyl-substituted amines, and mono- and di-alkenyl-substituted amines, and amines having one or more N-alkenyl substituent and N-alkyl substituent. Specific examples of such monoamines include n-butylamine, di-n-butylamine, allylamine, isobutylamine, cocoamine, stearylamine, laurylamine, methyllaurylamine, oleylamine, N-methyl-octylamine, dodecylamine, and octadecylamine. Examples of cycloaliphatic-substituted aliphatic amines, aromatic-substituted aliphatic amines, and heterocyclic-substituted aliphatic amines, include 2-(cyclohexyl)ethylamine, benzylamine, phenethylamine, and 3-(furyl-propyl)amine.

Cycloaliphatic monoamines are those monoamines wherein there is one cycloaliphatic substituent attached directly to the amino nitrogen through a carbon atom in the cyclic ring structure. Examples of cycloaliphatic monoamines include cyclohexylamines, cyclopentylamines, cyclohexenylamines, N-ethyl-cyclohexylamine, dicyclohexylamines, and the like. Examples of aliphatic-substituted, aromatic-substituted, and heterocyclic-substituted cycloaliphatic monoamines include propyl-substituted cyclohexylamines, phenyl-substituted cyclopentylamines, and pyranyl-substituted cyclohexylamnine.

Aromatic amines include those monoamines wherein a carbon atom of the aromatic ring structure is attached directly to the amino nitrogen. The aromatic ring will usually be a mononuclear aromatic ring (i.e., one derived from benzene) but can include fused aromatic rings, especially those derived from naphthalene. Examples of aromatic monoamines include substituted anilines, di-(paramethylphenyl)amine and naphthylamine. Examples of aliphatic-substituted, cycloaliphatic-substituted and heterocyclic-substituted aromatic monoamines are para-ethyoxyaniline, para-dodecylaminiline, cyclohexyl-substituted naphthylamine, and thienyl-substituted aniline.

Among the suitable nitrogen compounds are the polyamines. The polyamine may be aliphatic, cycloaliphatic, heterocyclic or aromatic. Examples of the polyamines include alkylene polyamines, N-alkylated alkylene polyamines, hydroxy containing polyamines, arylpolyamines, and heterocyclic polyamines.

N-alkylated alkylene polyamines are represented by the formula

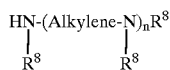

wherein n has an average value from 1, or 2 to 10, or to 7, or to 5, and the "Alkylene" group has from 1, or 2 to 10, or to 6, or to 4 carbon atoms. Each $R^8$ is independently hydrogen, or an aliphatic or hydroxy-substituted aliphatic group of up to 30 carbon atoms with the proviso that at least one $R^8$ is an aliphatic group of up to 30 carbon atoms. Additionally, within the repeating unit

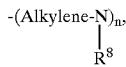

when n is 2 or more, the $R^8$ is independently hydrogen, or an aliphatic or hydroxy-substituted aliphatic group of up to 30 carbon atoms.

Such N-alkylated alkylenepolyamines can be prepared from polyamines such as ethylenepolyamines, butylenepolyamines, propylenepolyamines, pentylenepolyamines, etc. The higher homologs and related heterocyclic amines such as piperazines and N-aminoalkyl-substituted piperazines are also included. Specific examples of such polyamines are ethylenediamine, diethylenetriamine (DETA), triethylenetetramine (TETA), tris-(2-aminoethyl) amine, propylenediamine, trimethylenediamine, tripropylenetetramine, tetraethylenepentamine, hexaethyleneheptamine, pentaethylenehexamine, etc.

Higher homologs obtained by condensing two or more of the above-noted alkylene amines are similarly useful as are mixtures of two or more of the aforedescribed polyamines.

Ethylenepolyamines, such as those mentioned above, are useful. Such polyamines are described in detail under the heading Ethylene Amines in Kirk Othmer's "Encyclopedia of Chemical Technology", 2d Edition, Vol. 7, pages 22–37, Interscience Publishers, New York (1965). Such polyamines are most conveniently prepared by the reaction of ethylene dichloride with ammonia or by reaction of an ethylene imine with a ring opening reagent such as water, ammonia, etc. These reactions result in the production of a complex mixture of polyalkylenepolyamines including cyclic condensation products such as the aforedescribed piperazines. Ethylenepolyamine mixtures are useful.

Other useful types of polyamines mixtures are those resulting from stripping of the above-described polyamine mixtures to leave as residue what is often termed "polyarnine bottoms". In general, alkylenepolyamine bottoms can be characterized as having less than two, usually less than 1% (by weight) material boiling below about 200° C. A typical sample of such ethylene polyamine bottoms obtained from the Dow Chemical Company of Freeport, Tex. designated "E-100" has a specific gravity at 15.6° C. of 1.0168, a percent nitrogen by weight of 33.15 and a viscosity at 40° C. of 121 centistokes. Gas chromatography analysis of such a sample contains about 0.93% "Light Ends" (most probably DETA), 0.72% TETA, 21.74% tetraethylene pentamine and 76.61% pentaethylenehexamine and higher (by weight). These alkylenepolyamine bottoms include cyclic condensation products such as piperazine and higher analogs of diethylenetriamine, triethylenetriaamine and the like.

Useful substrates for this invention may be made from the abovedescribed polyamines by acylating with acylating agents such as long chain mono carboxylic acids or esters wherein the chain length is typically from about 12 carbon atoms up to about 30 carbon atoms. Additionally, the acylating agent may be a hydrocarbyl succinic acid or anhydride or ester acylating agent. Within the hydrocarbyl succinic acid or anhydride, two chain lengths are envisioned for the hydrocarbyl groups, one is a chain length of from 12 to 50 carbon atoms and the other is a chain length of from 70 to 300 carbon atoms.

In an especially preferred embodiment, the metal overbased amine is represented by the structure $$R^1R^2NH(MA)_x$$

wherein $R^2$ is hydrogen or $(CH_2)_3NH_2$, $R^1$ is an aliphatic group containing from 10 to about 50 carbon atoms and preferably from 12 to 26 carbon atoms or $R^4NH(CH_2)_3$ wherein $R^4$ is an aliphatic group containing from 10 to about 50 carbon atoms and preferably from 12 to 26 carbon atoms, M is a metal, A is carbonate, sulfite, sulfate, thiosulfate, phosphite or phosphate and x has a value of from 1.1 to 40. The metal overbased amine is prepared from an amine of the structure $R^1R^2NH$ wherein $R^1$ and $R^2$ are as defined above.

These especially preferred amines for this embodiment for overbasing include aliphatic monoamines, aliphatic diamines and aliphatic triamines. Based upon the parameters of the amine substituents, three different types of amines can be generated even though it would appear that four different amines could be generated.

When $R^2$ is hydrogen and $R^1$ is an aliphatic group, the amine structure is $$C_{10-50}\ \text{aliphatic} -NH_2$$

which defines fatty primary amines. A non-exhaustive, but exemplary list of fatty amines are decylamine, undecylamine, dodecylamine, tridecylamine, tetradecylamine, pentadecylamine, hexadecylamine, heptadecylamine, octadecylamine, oleylamine, etc.

For the second amine, when $R^2$ is $(CH_2)_3\ NH_2$ and $R^1$ is an aliphatic group, the amine structure is $$C_{10-50}\ \text{aliphatic}\ NH(CH_2)_3\ NH^2.$$

This structure is N-aliphatic trimethylenediamine and is available from AKZO as Duomeen™ O, Duomeen™ T and Duomeen ™ C.

When $R^2$ is hydrogen and $R^1$ is $R^4NH(CH_2)_3$, a different selection from the previous amines, the structure of the amine is $$C_{10-50}\ \text{aliphatic}\ NH(CH_2)_3\ NH_2$$

which is still N-aliphatic trimethylenediamine. The need for different values or parameters to generate the same amine will be appreciated later in this disclosure.

For the third amine, when $R^2$ is $(CH_2)_3NH_2$ and $R^1$ is $R^4NH(CH_2)_3$, the amine structure is $$C_{10-50}\text{aliphatic}\ (NH(CH_2)_3NH(CH_2)_3NH_2.$$

This structure is N-aliphatic dipropylenetriamine and is available from AKZO as Trimeen™ T.

The amount of amine in the final metal overbased amine component (A) including the reaction medium (described below), is typically 10 to 40 percent by weight, preferably 15 to 30 percent, and more preferably 20 to 30 percent.

The amine described above is, or becomes, through the present invention, a substrate of an overbased material. Conventional overbased materials are well known in the lubricating arts, and are generally single phase, homogeneous Newtonian systems characterized by a metal content in excess of that which would be present according to the stoichiometry of the metal and the particular acidic organic compound reacted with the metal. The metal overbased amine (A) differs from those of the prior art in that, in place of the acidic organic compound there is employed a non-acidic, non-reactive compound containing nitrogen atom(s), as described in detail above.

The amount of excess metal is commonly expressed in terms of metal ratio. The term "metal ratio" is the ratio of the total equivalents of the metal to the equivalents of the acidic organic compound. A neutral metal salt has a metal ratio of one. A salt having 4.5 times as much metal as present in a normal salt will have metal excess of 3.5 equivalents, or a ratio of 4.5. For the present invention, of course, this acidic material is not employed. However, a metal ratio can be defined, by analogy, to be the ratio of the total equivalents of the metal to the moles of nitrogen, oxygen, and sulfur atoms in the organic compound. The overbased (A) of the present invention typically contain 1.1 to 40 equivalents of metal per mole of amine (metal ratio) and preferably 5 to 25 equivalents of metal per mole of amine. In the metal overbased amine formula of $R^1R^2NH(MA)_x$, x represents the metal ratio.

The basicity of the overbased (A) generally is expressed in terms of a total base number. A total base number is the amount of acid (perchloric or hydrochloric) needed to neutralize all of the overbased material's basicity. The amount of acid is expressed as potassium hydroxide equivalents. Total base number is determined by titration of one gram of overbased material with 0.1 normal hydrochloric acid solution using bromophenol blue as an indicator. The overbased (A) of the present invention generally has a total base number of at least 20, preferably 100, more preferably 200. The overbased (A) generally has a total base number up to 600, preferably up to 500, more preferably up 400. The equivalents of overbased (A) is determined by the following equation: equivalent weight=(56,100/total base number). For instance, an overbased (A) with a total base number of 200 has an equivalent weight of 280.5 (eq. wt.=56100/200). The equivalent weight of amines is determined by dividing the molecular weight of the amine by the number of nitrogen atoms in the amine.

The overbased materials of the present invention are prepared by reacting an acidic material (typically an inorganic acid or lower carboxylic acid such as acetic acid; preferably carbon dioxide) with a mixture comprising the amine described in detail above, a reaction medium, a stoichiometric excess of a metal base M, and a promoter.

The metal compounds M useful in making the basic metal salts are generally any Group 1a or 1b metal compounds (CAS version of the Periodic Table of the Elements). The Group 1a metals of the metal compound include alkali metals (lithium, sodium, potassium, etc.). The Group 2a metals of the metal base include the alkaline earth metals (such as barium and, preferably, magnesium and calcium). Generally the metal compounds are delivered as metal salts. The anionic portion of the salt is hydroxyl, oxide, carbonate, borate, nitrate, other such anions or mixtures thereof.

An acidic material is used to accomplish the formation of the basic metal salt (MA). The acidic material reacts with the metal base to form (MA). The acidic material may be a liquid such as acetic, nitric, phosphoric, or sulfuric acids. Inorganic acidic materials in a solid or gaseous phase may also be used, such as HCl, $SO_2$, $S_3$, $CO_2$, $H_2S$, or $P_2O_5$. Some of the preceding materials are not technically acids, but anhydrides which become acids in the presence of a protic material such as water. Preferred acidic materials are carbon dioxide, sulfur dioxide, sulfur trioxide, phosphorus pentoxide or mixtures thereof. Most preferably, the acidic material is a gas such as carbon dioxide. The acidic material can be envisioned as AH and the metal base as MOH $$MOH + AH \rightarrow MA + H_2O$$

Typically about 1 equivalent of acidic material is employed per equivalent of the metal base.

Several representative examples of the formation of the x equivalents of the basic metal salt $(MA)_x$ from x equivalents of the metal base MOH and x equivalents of the acidic material AH are as follows. It is understood that before $CO_2$ and $SO_2$ act as an acidic material that $CO_2$ and $SO_2$ react with water present in the reaction vessel to form $H_2CO_3$ and $H_2SO_3$, respectively. It is also understood that calcium oxide is reacted with water present in the reaction vessel to form calcium hydroxide.

| 1 equivalent MOH | 1 equivalent + AH | 1 equivalent ? (MA) |
|---|---|---|
| NaOH | + ½$H_2CO_3$ | ? ½$Na_2CO_3$ |
| LiOH | + ½$H_2SO_3$ | ? ½$Li_2SO_3$ |
| ½$Ca(OH)_2$ | + ½$H_2CO_3$ | ? ½$CaCO_3$ |
| ½CaO | + ½$H_2CO_3$ | ? ½$CaCO_3$ |
| NaOH | + ⅓$H_3PO_4$ | ? ⅓$Na_3PO_4$ |
| ½$Ca(OH)_2$ | + ⅓$H_3PO_4$ | ? ¹⁄₁₆$Ca_3(PO_4)_2$ |

When one equivalent of an amine $R^1R^2NH$ is present in the reaction of x equivalents of MOH with x equivalents of AH, the reaction is $$R^1R^2NH + x\ MOH + x\ AH \rightarrow R^1R^2NH\ (MA)_x$$

Mixtures of acidic materials can also be used. This gives rise to an A within $R^1R^2NH(MA)_x$ of a carbonate, sulfite, sulfate, thiosulfate, phosphite and phosphate as well as mixtures thereof. Preferably A is carbonate.

A promoter is a chemical employed to facilitate the incorporation of metal into the basic metal compositions. The promoters are quite diverse and are well known in the art, as evidenced by the cited patents. A particularly comprehensive discussion of suitable promoters is found in U.S. Pat. Nos. 2,777,874, 2,695,910, and 2,616,904. These include the alcoholic and phenolic promoters, which are preferred. The alcoholic promoters include the alkanols of one to twelve carbon atoms such as methanol, ethanol, amyl alcohol, octanol, isopropanol, and mixtures of these and the like. Phenolic promoters include a variety of hydroxy-substituted benzenes and naphthalenes. A particularly useful class of phenols are the alkylated phenols of the type listed in U.S. Pat. No. 2,777,874, e.g., heptylphenols, octylphenols, and nonylphenols. Mixtures of various promoters are sometimes used.

The reaction medium in which the above overbasing reaction is conducted comprises at least one inert, organic solvent (mineral oil, naphtha, toluene, xylene, etc.) for the amine. Preferably the medium is an oil such a mineral oil; alternatively it can be a volatile organic solvent. The use of a volatile organic solvent can be desirable when it is intended to strip off the solvent to replace it with an alternative solvent or even to isolate the remaining solids. The amount of the reaction medium should be an amount suitable to provide ready solution or dispersion of the other components during the process of preparing the overbased material. Typically the reaction medium will comprise 15 to 60 percent by weight of the total composition, preferably 25 to 50 percent, and more preferably 30 to 40 percent.

The reaction medium, however, should be a material which does not form a soluble salt of the metal base described above. The function of providing a measure of solubility to the metal base, so that it can participate in the overbasing reaction, is accomplished by the use of a catalytic amount of an organic material which is capable of forming a salt with the metal base. The salt formed thereby should be soluble in the reaction medium. This organic material can be an acidic material such as a carboxylic acid, sulfonic acid, phosphorous acid, preferably an alkyl substituted succinic acid or anhydride, or an alkylphenol. The amount of this organic material (the acidic material, for example) is described as a "catalytic amount," by which is meant a relatively small amount sufficient to permit incorporation of the metal into the composition in association with the amine. The amount will not be so large that the acidic material itself begins to serve as the primary or a significant substrate for the overbasing process. These suitable amounts are typically 0.01 to 5 percent by weight of the total composition, and preferably 0.5 to 2 percent. Expressed in another fashion, the amount of the acidic organic material is typically 0.05 to 25 percent by weight of the amine containing the oxygen, nitrogen, or sulfur, which is being overbased. Preferably the amount of the acidic organic material up to 15 percent by weight, preferably up to 9 percent, and more preferably up to 6 percent, e.g., 2–6 percent by weight of the amine.

Patents specifically describing techniques for making basic salts of acids include U.S. Pat. Nos. 2,501,731; 2,616,905; 2,616,911; 2,616,925; 2,777,874; 3,256,186; 3,384,585; 3,365,396; 3,320,162; 3,318,809; 3,488,284; and 3,629,109. Reference may be made to these patents for their disclosures in this regard as well as for their disclosure of specific suitable basic metal salts. The teachings, of course, must be modified as appropriate for the use of the amines of the present invention in place of the acids described in the references.

Briefly, the basic salts of the amines of the present invention are prepared by preparing a mixture of the amine, the reaction medium, the metal base, and the salt-forming organic material, and adding thereto the appropriate amount of the low molecular weight acidic material, that is, one preferably containing no more than 6 carbon atoms. Liquid or solid acidic materials can be added to a stirred mixture by conventional means; gaseous acidic materials can be added by passing the gas (bubbling the gas) into a stirred reaction mixture. The temperature of the addition of gas is not critical; temperatures in the range of 100 to 150° C. have been found to be quite suitable. The reaction can be done in a single step or incrementally.

Once an overbased amine is obtained it can be further treated or reacted, as desired. Carbonate overbased amines $R^1R^2NH(MA)_x$ wherein A is carbonate (i.e., those prepared by reaction with carbon dioxide) can be reacted with a source of sulfur dioxide to provide a sulfite overbased material wherein A is sulfite. During the course of the reaction, some or all of the carbon dioxide will be displaced by the sulfur dioxide. In another modification, sulfite overbased material (prepared either by direct addition of $SO_2$ or by $SO_2$ displacement of $CO_2$) can be further reacted with a source of sulfur to provide a thiosulfate overbased material wherein A is thiosulfate. Suitable sources of sulfur include elemental sulfur, sulfur halides, combinations of sulfur or sulfur oxides with hydrogen sulfide, phosphorus sulfides, and various sulfurized organic compounds. Sulfur halides include sulfur monochloride and sulfur dichloride. Phosphorus sulfides include phosphorus pentasulfide, $P_4S_7$, $P_4S_3$, and P2S3. Sulfurized organic compounds include 2,2'-dithiodiisobutyraldehyde, dibenzyl sulfide, dixylyl sulfide, dicetyl sulfide, diparaffin wax sulfide and polysulfide, and cracked wax oleum sulfides sulfurized oils, and sulfurized fatty acids. Additional sulfur sources, and methods of their preparation, can be found by referring to European Publication 0 586 258. The conversion of carbonate overbased salts of conventional acid substrates into sulfite overbased materials has been disclosed in detail in U.S. Pat. No. 5,250,204. Further details on the conversion of sulfite overbased salts of conventional acid substrates into thiosulfate overbased materials can be obtained by referring to European Publication 0 586 258.

As used herein, the term "hydrocarbyl substituent" or "hydrocarbyl group" is used in its ordinary sense, which is well known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

The term "hydrocarbyl" is also intended to include hydrocarbylene, that is, groups having non-hydrocarbon functionality at multiple ends.

As stated earlier, based upon the parameters of the amine substituents of the especially preferred amine, three different types of amines can be generated even though it would appear that four different amines could be generated. Further, a selection of different values generates the same two amines—the N—aliphatic trimethylenediamines. However, by the factoring in of the $(MA)_x$ moiety—that is, for diamines, which nitrogen atom is associated with or aligns with the $(MA)_x$ moiety—one readily can determine that five different overbased amines can be generated. an aliphatic group, the overbased amine structure is

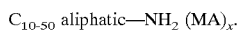

$C_{10\text{-}50}$ aliphatic—$NH_2$ $(MA)_x$.

This is an overbased primary fatty amine wherein the overbased moiety $(MA)_x$ is aligned with the primary amine, the only amine present.

In the structure $R^1R^2NH(MA)_x$, when $R^2$ is $(CH_2)_3NH_2$ and $R^1$ is an aliphatic group, the overbased amine structure is

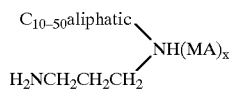

wherein the overbased moiety $(MA)_x$ is aligned with the secondary amine.

In the structure $R^1R^2NH(MA)_x$ when $R^2$ is hydrogen and $R^1$ is $R^4NH(CH_2)_3$
wherein $R^4$ is an aliphatic group, the overbased amine structure is

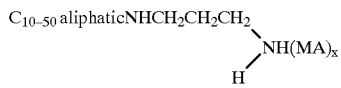

wherein the overbased moiety $(MA)_x$ is aligned with the primary amine.

In the structure, $R^1R^2NH(MA)_x$ when $R^2$ is $(CH_2)_3NH_2$ and $R^1$ is $R^4NH(CH_2)_3NH_2$, wherein $R^4$ is an aliphatic group. The overbased amine structure is

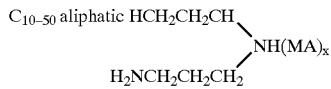

wherein the overbased moiety $(MA)_x$ is aligned with the secondary amine.

Finally, when at least two nitrogen atoms are present in the amine, the metal may be aligned with any two of the nitrogen atoms, as in chelation.

Preparation of the Metal Overbased Amine (A)

Example A1

To a 2 L flask is charged 175 g tallowdiaminopropane, 150 g mineral oil, 30 g polyisobutylene-substituted succinic anhydride and 27 g propylene tetramer-substituted phenol. The mixture is heated to 50–60° C. and 42 g lithium hydroxide monohydrate is added, with stirring. Carbon dioxide is blown into the mixture at 28 L/hr (1.0 std. ft³/hr) for 2 hours at 120–130° C. (the exothermic reaction increases the temperature to 170–180° C.). Infrared analysis shows the formation of $Li_2CO_3$. A second charge of 42 g lithium hydroxide monohydrate is added and the mixture carbonated as above, followed by addition of a third charge of 42 g lithium hydroxide and carbonation. To the resulting viscous oil is added hexane diluent, the mixture centrifuged and filtered through filter aid, then vacuum stripped to yield 350 g light brown oil.

Example A2

To a 1 L flask is charged 175 g tallowdiaminopropane, 150 g mineral oil, 20 g of calcium salt of methylene-coupled heptyl phenol, 20 g polyisobutylene-substituted succinic anhydride, 50 g mixed isobutyl and amyl alcohols (1:1), and 12 g methanol. In this mixture is dissolved, with stirring, 2 g calcium chloride and 8 g water; to this mixture is added, with stirring, 37 g calcium hydroxide. The mixture is heated to 50° C. and carbon dioxide is blown into the reaction mixture at 28 L/hr (1.0 std. ft³/hr) for 2 hours, maintaining the temperature at about 50–60° C. After 2 hours, infrared analysis indicates formation of calcium carbonate. An additional 18 g of calcium hydroxide is added and carbonation is continued for an additional 2.5 hours. The mixture is then purged with nitrogen at 150° C. and the solvent is removed by distillation followed by vacuum stripping for 0.5 hours. The mixture is filtered using a filter aid, to yield 360 g of a green oil product.

Example A3

To a 1 L flask is charged 175 g tallowdiaminopropane, 100 g mineral oil, 25 g polyisobutylene-substituted succinic anhydride, and 20 g propylene tetramer-substituted phenol. To this mixture is added, with stirring, 20 g sodium hydroxide at 50° C., followed by the addition of three portions of phosphorus pentoxide over a time period of 1.5 hours. The reaction, being exothermic, heats spontaneously to about 80° C. Stirring is continued for about 1 hour, followed by cooling to room temperature. An additional charge of 40 g sodium hydroxide is added at 50° C., followed by two portions of 17.5 g each phosphorus pentoxide, over a course of about 0.5 hour. After an additional hour of stirring, and additional charge of 17.5 g phosphorus pentoxide is added, at a temperature of about 90° C., then, after an additional 0.5 hours, a final charge of 17.5 g phosphorus pentoxide is added. Stirring is continued for 3 hours. Product is isolated as previously described.

Example A4

A 12 L flask is charged with 700 g (2.0 mole) N-oleyl-1,3-diaminopropane, 150 g (0.22 mole) polyisobutylene substituted succinic anhydride, 150 g (0.54 mole) propylene tetramer-substituted phenol and 800 g mineral oil. The mixture is heated to 50° C. and 280 g of sodium hydroxide is added. The temperature is increased to 135–140° C. and into this mixture is blown carbon dioxide at 1.75 cubic feet per hour for 5 to 6 hours. Water is collected in a Dean Stark trap where 26 g is obtained. The contents are cooled to 100° C. and the second increment of sodium hydroxide—320 g is added and the contents are carbonated as per above. A third increment—320 g and a fourth increment 280 g are added and both of these increments are carbonated as above. A total of 215 g is obtained in the Dean Stark trap. The contents are stripped to 150° C. and 20 millimeters mercury for 0.5 hours until no additional water is obtained. The contents are filtered through filter aid at 120–130° C. to give 2675 g of a light brown product. Analyses: % sodium is 22; % ash is 49; % nitrogen is 1.58. In the formula $R^1R^2NH(MA)_x$, M is sodium, A is carbonate and x is 15.

Example A5

Example A4 is essentially repeated but at a lower conversion. In the formula $R^1R^2NH(MA)_x$, M is sodium, A is carbonate and x is 5.

Example A6

To a 2 liter flask is charged 1029 g (7.0 equivalents) of the product of Example A4. The contents are heated to 140° C. and $SO_2$ is blown below the surface at 0.5 cubic feet per hour for 5 hours, until the disappearance of the sodium carbonate band on the IR at 880 $cm^{-1}$ is observed. Nitrogen is then blown below the surface for 1 hour. The contents are filtered to give a product that has a % sodium of 9.6, and % sulfur of 8.0. In the formula $R^1 R^2NH(MA)_x$, M is sodium, A is sulfite and x is 5.0.

Example A7

To a 1 liter flask it charged 400 g (1.0 equivalent) of the product of Example A5. Added is 26 g (0.8 equivalents) of sulfur over 20 minutes. A thick thiosulfate oil is formed. Added is 200 ml toluene and the contents are heated to reflux and held for 1 hour. The contents are filtered to give a product having a % sodium of 8.9 and % sulfur of 12.9. In the formula $R^1R^2NH(MA)_x$, M is sodium, A is thiosulfate and x is 5.0.

Example A8

To a 2 liter flask is charged 1700 g (15.7 equivalents) of the product of Example A4 and 340 g diluent oil. The contents are heated to 100° C. and $SO_2$ is blown below the surface at 1.5 cubic feet per hour at 100–120° C. for 10 hours until the disappearance of the sodium carbonate on the IR at 880 $cm^{-1}$ is observed. The contents are then purged with nitrogen below the surface at 1 cubic foot per hour for 1 hour. The contents are filtered to give a product having a % sodium of 14.3 and % sulfur of 11.8 and x of 15.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil which may be customarily present in the commercial material, unless otherwise indicated. As used herein, the expression "consisting essentially of" permits the inclusion of substances which do not materially affect the basic and novel characteristics of the composition under consideration.

(B) The Amine Derivitizing Aoent

The metal overbased amine (A) is an intermediate and as such, it is reacted with various amine derivitizing agents to form antiwear/extreme pressure derivatives of metal overbased amine derivatives. Amines, when reacted with certain reagents, will form a specific derivative. It is no different with overbased amines. The overbased portion of the overbased amine does not enter into the reaction. The overbased portion acts as a spectator. Only the amine undergoes reaction with the reagents. Amine derivitizing agents having utility in this invention are carbon disulfide and phosphorus pentoxide. The reaction of the metal overbased amine (A) and amine derivitizing agent (B) is conducted at a temperature of from ambient up to about 150° C.

Two different sulfur derivatives are envisioned in this invention. The first sulfur derivative (I) is formed by the reaction of one mole of the metal overbased amine with at least one mole of carbon disulfide (B1). While not wishing to be bound by theory, it is believed that the $(MA)_x$ is associated with the nitrogen, regardless of where it is drawn.

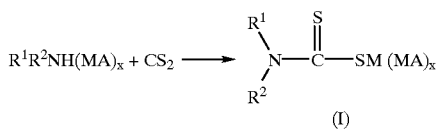

The second sulfur derivative (II) is formed by the reaction of one mole of the metal overbased amine with at least one mole of carbon disulfide and at least one mole of an acrylate ester. The acrylate ester is of the formula $CH_2=CR^5COOR^6$ wherein $R^5$ is hydrogen or a methyl group and $R^6$ is an alkyl group that contains from 1 to 4 carbon atoms.

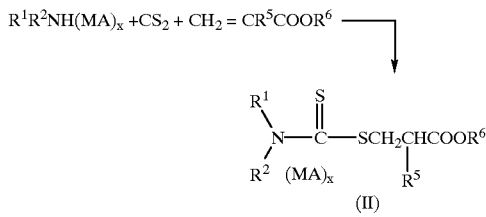

(II)

In preparing the sulfur derivatives (I) and (II), an excess of carbon disulfide per one mole of the metal overbased amine, or an excess of carbon disulfide with an excess of acrylate ester per one mole of metal overbased amine is employed.

Examples directed to the preparation of the sulfur derivatives are as follows: Preparation of (I)

EXAMPLE 1

Charged to a 0.5 liter flask is 30 g (0.4 mole) of carbon disulfide. A solution of 172 g (0.2 equivalents) of sodium carbonate overbased N-oleyl-1,3-diaminopropane of Example A4 and 100 ml of hexanes is prepared. The prepared solution is added dropwise to the carbon disulfide while stirring. The contents are stirred for 3 hours at room temperature and at 30° C. for 0.5 hours. The solvent was removed by distillation to 1 10° C. and 30 mm of mercury to give a product having % sodium of 17.7, % sodium ash of 55.2 and % sulfur of 2.4. Preparation of (1:)

EXAMPLE 2

Charged to a 0.5 liter is 156 g (0.15 equivalents) of the product of Example A8 in 100 g hexane. The contents are stirred and added is 15 g (0.15 equivalents) of methyl acrylate and 23 g (0.3 mole) of carbon disulfide at room temperature in 15 minutes. The contents are heated to 50–60° C. for 1 hour and then to 85° C. for 1 hour. Solvent and excess carbon disulfide is removed at 120° C. until no further volatiles are distilled. The thick liquid in the flask is the product.

A phosphorus derivative (III) is formed by first reacting one mole of the metal overbased amine with at least one mole of (B2) an epoxide to form one mole of an intermediate and reacting the intermediate with at least 0.33 moles of phosphorus pentoxide. The epoxide is of the formula

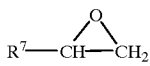

wherein $R^7$ is hydrogen or an alkyl group that contains from 1 to 4 carbon atoms and preferably 1 carbon atom.

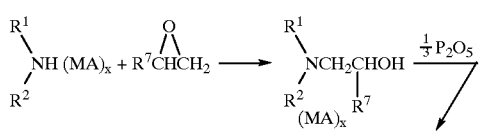

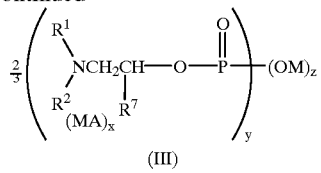

(III)

In the above (E), the sum of y and z are 3.

In preparing the phosphorus derivative (III), an excess of epoxide per one mole of the metal overbased amine is employed to form one mole of an intermediate which is then reacted with at least 0.33 moles of phosphorus pentoxide.

Examples directed to the preparation of the phosphorus derivatives (E) are as follows:

EXAMPLE 3

A precursor for the preparation of (III) for Example 3 is made by adding to a 1 liter flask 515 g (1.0 equivalent) of sodium carbonate overbased N-oleyl-1,3-diaminopropane of Example A5. Added in a dropwise manner is 144 g (2.0 equivalents) of butylene oxide in 30 minutes. The contents are stirred at 50° C. for 16 hours. The contents are stripped to 120° C. at 25 mm mercury to give a product having % sodium of 9.0 and a total base number of 349.

A mixture of 300 g (0.51 equivalents) of the EXAMPLE 3 precursor and 25 g (0.34 equivalents) of phosphorus pentoxide is stirred at 40° C. for 8 hours. The addition of the phosphorus pentoxide is exothermic and the temperature rises to 60–70° C. At the end of the reaction time, the contents are filtered at 50° C. to give a product having % sodium of 7.4, % phosphorus of 2.74 and a total base number of 258.

EXAMPLE 4

A precursor for the preparation of (E) for Example 4 is made by adding to a 1 liter flask is 475 g (0.85 equivalents) of sodium sulfite overbased N-oleyl-1,3-diaminopropane of Example A6. While stirring, 92 g (1.28 equivalents) of butylene oxide is added. The contents are stirred at 50–60° C. for 3 hours. The excess butylene oxide is removed by distillation at 130° C. and 20 mm mercury to give a product having a % sodium of 8.8 and a % sulfur of 7.3.

A mixture of 510 g (0.81 equivalents) of the Example 4 precursor and 38.5 g (0.54 equivalents) of phosphorus pentoxide are stirred at 50° C. for 3.54 hours. The contents are diluted with 150 g toluene and filtered. The filtrate is stripped to remove the toluene at 100° C. and 20 mm mercury to give a product having a % sodium of 7.9, % sulfur of 6.6 and % phosphorus of 3.1.

EXAMPLE 5

A precursor for the preparation of (III) for Example 5 is made by adding 563 g (0.73 equivalents) of the product from Example A7 in 300 ml toluene. Stirring is begun and 79 g (1.1 moles) butylene oxide is added in 15 minutes. The temperature is increased to 40° C. and held for 5 hours. The contents are distilled to give the precursor.

A mixture of 585 g (0.64 equivalents) of the Example 5 precursor and 30 g (0.43 equivalents) of phosphorus pentoxide are stirred at 40° C. for 0.75 hours. The mixtures exotherms to 55° C. The contents are stirred for 16 hours at room temperature and then stripped to 140° C. and 20 mm mercury. The contents are filtered to give a product having a % sodium of 5.8, % sulfur of 10.7 and % phosphorus of 2.03.

A sulfur-phosphorus derivative (IV) is formed by reacting one mole of (I) above with at least one mole of (B3) an epoxide to form one mole of an intermediate and reacting the intermediate with at least 0.33 moles of phosphorus pentoxide. The epoxide is the same as used in the formation of the intermediate for the preparation of (III) above.

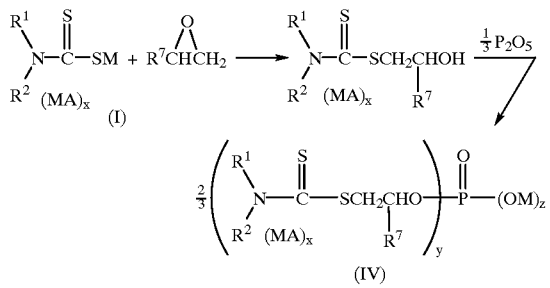

In the above (IV), the sum of y and z are 3.

In preparing the sulfur-phosphorus derivative (IV), an excess of epoxide per one mole of metal overbased amine sulfur derivative (I) is employed to form one mole of an intermediate which is then reacted with at least 0.33 moles of phosphorus pentoxide.

Examples directed to the preparation of the sulfur-phosphorus derivatives (IV) are as follows:

EXAMPLE 6

A precursor for the preparation of (IV) for Example 6 is made by adding to a 0.5 liter flask 23 g (0.3 moles) carbon disulfide and 7.2 g (0.1 equivalent) of butylene oxide. At 10° C. is added 55.2 g (0.06 equivalent) of the product of Example A4 in 100 g hexane in 30 minutes. The contents are stirred for 3 hours at room temperature. The solvent and excess carbon disulfide and butylene oxide is stripped at 120° C. until no further volatiles are obtained. The thick liquid in the flask is the precursor product having a % sodium of 16.0 and % sulfur of 5.7.

A mixture of 53 g (0.05 equivalents) of the Example 6 precursor and 2.4 g (0.017 moles) of phosphorus pentoxide are added and stirred at 80–90° C. for 3 hours and then to 110° C. for 30 minutes. The contents are filtered to give a product having % sodium of 15, % sulfur of 5.4 and % phosphorus of 1.8.

The materials of the present invention are useful as additives for lubricants in which they can function as conventional overbased detergents; they can also function as antiwear, antiweld, antioxidation, antifriction, antirust, anticorrosion, and/or extreme pressure agents. They may be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic or manual transmission fluids, transaxle lubricants, gear lubricants, including open and enclosed gear lubricants, tractor lubricants, metal-working lubricants, hydraulic fluids and other lubricating oil and grease compositions can also benefit from the incorporation therein of the compositions of the present invention. They may also be used as wirerope, walking cam, way, rock drill, chain and conveyor belt, worm gear, bearing, metalworking, and rail and flange lubricants, and as lubricants in industrial fluids in general, whether oil or water base.

As described above, the formulated lubricating composition contains an oil of lubricating viscosity. The oils of lubricating viscosity include natural or synthetic lubricating oils and mixtures thereof. Natural oils include animal oils, mineral lubricating oils, and solvent or acid treated mineral oils. Synthetic lubricating oils include hydrocarbon oils (polyalpha-olefins), halo-substituted hydrocarbon oils, alkylene oxide polymers, esters of dicarboxylic acids and polyols, esters of phosphorus-containing acids, polymeric tetrahydrofurans and silicon-based oils. Preferably, the oil of lubricating viscosity is a hydrotreated mineral oil or a synthetic lubricating oil, such as a polyolefin. Examples of useful oils of lubricating viscosity include XIVI basestocks, such as 100N isomerized wax basestock (0.01% sulfur/141 VI), 120N isomerized wax basestock (0.01% sulfurl 149 VI), 170N isomerized wax basestock (0.01% sulfur/142 VI), and 250N isomerized wax basestock (0.01% sulfur/146 VI); refined basestocks, such as 250N solvent refined paraffinic mineral oil (0.16% sulfur/89 VI), 200N solvent refined naphthenic mineral oil (0.2% sulfur/60 VI), 100N solvent refined/ hydrotreated paraffinic mineral oil (0.01% sulfur/98 VI), 240N solvent refined/ hydrotreated paraffinic mineral oil (0.01% sulfur/98 VI), 80N solvent refined/ hydrotreated paraffinic mineral oil (0.08% sulfur/127 VI), and 150N solvent refined/ hydrotreated paraffinic mineral oil (0.17% sulfur/127 VI). A description of oils of lubricating viscosity occurs in U.S. Pat. No. 4,582,618.

In one embodiment, the oil of lubricating viscosity is a polyalpha-olefin (PAO). Typically, the polyalpha-olefins are derived from monomers having from 4 to 30, or from 4 to 20, or from 6 to 16 carbon atoms. Examples of useful PAOs include those derived from decene. These PAOs may have a viscosity from 3 to 150, or from 4 to 100, or from 4 to 8 cSt at 100° C. Examples of PAOs include 4 cSt polyolefins, 6 cSt polyolefins, 40 cSt polyolefins and 100 cSt polyalphaolefins.

In one embodiment, the lubricating composition contains an oil of lubricating viscosity which has an iodine value of less than 9. Iodine value is determined according to ASTM D-460. In one embodiment, the oil of lubricating viscosity has an iodine value less than about 8, or less than 6, or less than 4.

In one embodiment, the oil of lubricating viscosity are selected to provide lubricating compositions with a kinematic viscosity of at least 3.5 cSt, or at least 4.0 cSt at 100° C. In one embodiment, the lubricating compositions have an SAE gear viscosity grade of at least SAE 75W. The lubricating composition may also have a so-called multigrade rating such as SAE 75W-80, 75W-90, 75W-140, 80W-90, 80W-140, 85W-90, or 85W-140. Multigrade lubricants may include a viscosity improver which is formulated with the oil of lubricating viscosity to provide the above lubricant grades. Useful viscosity improvers include but are not limited to polyolefins, such as ethylene-propylene copolymers, or polybutylene rubbers, including hydrogenated rubbers, such as styrene-butadiene or styrene-isoprene rubbers; or polyacrylates, including polymethacrylates. In one embodiment, the viscosity improver is a polyolefin or polymethacrylate. Viscosity improvers available commercially include AcryloidTM viscosity improvers available from Rohm & Haas; Shellvis™ rubbers available from Shell Chemical; Trilenem polymers, such as Trilene™ CP-40, available commercially from Uniroyal Chemical Co., and Lubrizol 3100 series and 8400 series polymers, such as Lubrizol® 3174 available from The Lubrizol Corporation.

In one embodiment, the oil of lubricating viscosity includes at least one ester of a dicarboxylic acid. Typically the esters containing from 4 to 30, preferably from 6 to 24, or from 7 to 18 carbon atoms in each ester group. Here, as well as elsewhere, in the specification and claims, the range and ratio limits may be combined. Examples of dicarboxylic acids include glutaric, adipic, pimelic, suberic, azelaic and sebacic. Example of ester groups include hexyl, octyl, decyl, and dodecyl ester groups. The ester groups include linear as well as branched ester groups such as iso arrangements of the ester group. A particularly useful ester of a dicarboxylic acid is diisodecyl azelate.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. An antiwear/extreme pressure composition comprising; a metal overbased amine of the structure

wherein $R^1$ and $R^2$ are each independently hydrogen, or a hydrocarbyl group, amino-substituted hydrocarbyl group, hydroxy-substituted hydrocarbyl group, alkoxy-substituted hydrocarbyl group or amino groups wherein the hydrocarbyl group contains from 4 to 50 carbon atoms, provided that $R^1$ and $R^2$ are not both hydrogen, M is a metal, A is carbonate, sulfite, sulfate, thiosulfate, phosphite, phosphate, or mixtures thereof, and x has a value of from 1.1 to 40;

wherein said metal overbased amine is reacted with carbon disulfide to form a sulfur derivative of a metal overbased amine, an epoxide followed by phosphorus pentoxide to form a phosphorus derivative of a metal overbased amine or wherein the sulfur derivative is further reacted with an epoxide followed by phosphorus pentoxide to form a sulfur and phosphorus derivative of a metal overbased amine.

2. The composition of claim 1 wherein $R^2$ is hydrogen.
3. The composition of claim 2 wherein $R^1$ is an aromatic group.
4. The composition of claim 1 wherein $R^2$ is hydrogen or $(CH_2)_3NH_2$, $R^1$ is an aliphatic group containing from 10 to about 50 carbon atoms or $R^4NH(CH_2)_3$ wherein $R^4$ is an aliphatic group containing from 10 to about 50 carbon atoms.
5. The composition of claim 1 wherein the metal M comprises alkali or alkaline earth metals.
6. The composition of claim 1 wherein the alkali metals comprise lithium, sodium or potassium.
7. The composition of claim 1 wherein the alkaline earth metals comprise magnesium or calcium.
8. The composition of claim 4 wherein $R^1$ and $R^4$ are aliphatic groups containing from 12 to 26 carbon atoms.
9. The composition of claim 4 wherein $R^1$ and $R^4$ are oleyl groups.
10. The composition of claim 1 wherein the metal overbased amine is prepared from an N-alkylated polyamine of the formula

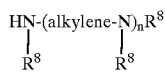

wherein each $R^8$ is independently hydrogen, or an aliphatic or hydroxy-substituted aliphatic group of up to 30 carbon atoms with the proviso that at least one $R^8$ is an aliphatic group of up to 30 carbon atoms, the alkylene group has from 1 to 10 carbon atoms and n is from 1 to 10 and that when n is 2 or more, the $R^8$-N-alkylene is independently hydrogen, or an aliphatic or hydroxy-substituted aliphatic group of up to 30 carbon atoms.

11. The composition of claim 1 wherein the metal overbased amine is prepared from an amine made by reacting a polyamine with an acylating agent.
12. The composition of claim 11 wherein the acylating agent is a long chain mono carboxylic acid or ester wherein the chain contains from 12 to 30 carbon atoms.
13. The composition of claim 11 wherein the acylating agent is a hydrocarbyl substituted succinic acid or anhydride acylating agent.
14. The composition of claim 11 wherein the hydrocarbyl group contains from 12 to 50 carbon atoms.
15. The composition of claim 11 wherein the hydrocarbyl group contains from 70 to 300 carbon atoms.
16. The composition of claim 1 wherein x is from 5 to 25.
17. The composition of claim 1 wherein the sulfur derivative of the metal overbased amine is represented by the structure

wherein $R^5$ is hydrogen or methyl and $R^6$ is an alkyl group that contains from 1 to 4 carbon atoms.

18. The composition of claim 1 wherein the phosphorus derivative of the metal overbased amine is represented by the structure

wherein $R^7$ is hydrogen, methyl or ethyl and y+z is 3.

19. The composition of claim 1 wherein the sulfur and phosphorus derivative of the metal overbased amine is represented by the formula

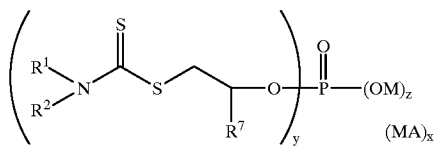

wherein $R^7$ is hydrogen, methyl or ethyl and y+z is 3.

20. The composition of claim 1 wherein A is carbonate.

21. The composition of claim 17 wherein (I) is formed by the reaction of $R^1R^2NH(MA)_x$ with carbon disulfide.

22. The composition of claim 17 wherein (II) is formed by the reaction of $R^1R^2NH(MA)_x$ with carbon disulfide and $CH_2{=}CR^5COOR^6$ wherein $R^5$ is hydrogen or methyl and $R^6$ is an alkyl group that contains from 1 to 4 carbon atoms.

23. The composition of claim 18 wherein (III) is formed by the reaction of $R^1R^2NH(MA)_x$ with

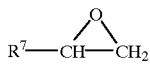

to form an intermediate and reacting, the intermediate with phosphorus pentoxide.

24. The composition of claim 19 wherein (IV) is formed by the reaction of

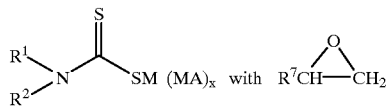

wherein $R^7$ is hydrogen, methyl or ethyl to form an intermediate and reacting the intermediate with phosphorus pentoxide.

25. A process for preparing antiwear/extreme pressure derivatives of metal overbased amines comprising reacting (A) one mole of a metal overbased amine of the structure $R^1R^2HN(MA)_x$ wherein $R^1$ and $R^2$ are each independently hydrogen, or a hydrocarbyl group, amino-substituted hydrocarbyl group, hydroxy-substituted hydrocarbyl group, alkoxy-substituted hydrocarbyl group or amino groups wherein the hydrocarbyl group contains from 4 to 50 carbon atoms, provided that $R^1$ and $R^2$ are not both hydrogen, M is a metal, A is carbonate, sulfite, sulfate, thiosulfate, phosphite, phosphate, or mixtures thereof, and x has a value of from 1.1 to 40; with (B) an amine derivatizing agent comprising
  (1) at least one mole of carbon disulfide to form a sulfur derivative of a metal overbased amine,
  (2) at least one mole of an epoxide followed by at least 0.33 moles of phosphorus pentoxide to form a phosphorus derivative of a metal overbased amine or
  (3) at least one mole of carbon disulfide followed by at least one mole of an epoxide followed by at least 0.33 moles of phosphorus pentoxide to form a sulfur and phosphorus derivative of a metal overbased amine, at a temperature of from ambient up to about 150° C.

* * * * *